United States Patent [19]

Ichikawa et al.

[11] Patent Number: 5,230,219
[45] Date of Patent: Jul. 27, 1993

[54] FREEZING METHOD AND APPARATUS

[75] Inventors: Michinori Ichikawa; Gen Matsumoto, both of Ibaraki; Yoshiro Hanyu, Tokyo; Hiroshi Takahashi, Ibaraki, all of Japan

[73] Assignees: Agency of Industrial Science and Technology, Tokyo; Eiko Engineering Co., Ltd., Ibaraki, both of Japan

[21] Appl. No.: 532,198

[22] Filed: Jun. 1, 1990

[30] Foreign Application Priority Data

Dec. 30, 1989 [JP] Japan .................................. 1-340024

[51] Int. Cl.$^5$ ............................................. F24F 3/16
[52] U.S. Cl. ............................................. 62/78; 62/264
[58] Field of Search ...................... 62/78, 264, 66, 340

[56] References Cited

U.S. PATENT DOCUMENTS

| 3,439,510 | 4/1969 | Gray | 62/264 |
|---|---|---|---|
| 3,470,942 | 10/1969 | Fukada et al. | 62/78 |
| 3,536,129 | 10/1970 | White | 62/264 |

Primary Examiner—Ronald C. Capossela
Attorney, Agent, or Firm—Flynn, Thiel, Boutell & Tanis

[57] ABSTRACT

The invention relates to a method and apparatus for freezing a sample by solidifying a liquid contained in the sample and widen the distance within the sample where the same is amorphously solidified. For this purpose, the sample is cooled immediately after being irradiated with an electromagnetic wave. The apparatus includes an electromagnetic irradiating means for irradiatine an electromagnetic wave on a sample immediately before freezing thereof.

3 Claims, 2 Drawing Sheets

FREEZING METHOD AND APPARATUS

BACKGROUND OF THE INVENTION

1. Field of the Invention

This invention relates to a freezing method and apparatus for freezing samples by solidifying liquid or fluid materials contained in the samples and more particularly, to a freezing which comprises a means for extending the region of a sample in which it is amorphously solidified.

2. Description of the Prior Art

When samples containing liquids therein, e.g. organism samples, are observed through electron microscope, it is the ususal practice to solidify the sample by quick freezing.

A typical apparatus of the above type is one shown in FIG. 3. In this apparatus, a sample 19 to be frozen is attached to the tip of a plunger 16. The sample 19 is manually, rapidly moved toward a pure copper block 18, which is placed in a Dewar 17 filled with a liquid helium refrigerant 20, until the surface of the sample 19 contacts the surface of the copper block 18. As a consequence, the heat energy of the sample 19 is absorbed by the copper block 18, facilitating quick freezing.

When the sample 19 containing a liquid is frozen, the tissue of the sample 19 is broken by the growth of ice crystals of the liquid. In order to freeze the sample 19 in such a state as it is, it is essential to suppress formation of ice crystals. In this regard, the known apparatus has been so designed that the copper block 18 is cooled to a very low temperature of about 10° K. so that the sample 19 is cooled at a rate as fast as possible. By this, the growth of ice crystals in the sample 19 is minimized, so that the water contained in the sample 19 is solidified in the form of amorphous ice, permitting the sample 19 to be kept as it is.

However, a above known quenching apparatus has the problem that the distance where water contained in the sample 19 is amorphously frozen is limited only to part of the sample 19 at approximately 20 um from its surface which contact the copper block 18.

For high freezing rates, use of liquid helium as a refrigerant is essential which makes it difficult to handle the apparatus because of additional operation costs. This is one of the great reasons for preventing the spread of freezesolidifying techniques.

SUMMARY OF THE INVENTION

It is an object of the invention to provide a method and apparatus for freezing samples containing liquids therein which overcome the drawbacks of the prior art method and apparatus.

In accordance with one embodiment of the invention, there is provided a method for quickly freezing a sample comprising of a liquid, a solid material containing a liquid or a liquid material containing solid matters, which comprises quickly freezing the sample immediately after irradiation with an electromagnetic wave.

According to another embodiment of the invention, there is also provided an apparatus for quickly freezing a sample comprising a liquid, a solid material containing a liquid or a liquid material containing solid matters, the apparatus comprising a sample support means for supporting the sample at a lower end thereof, the sample support means being vertically movable, a cooling unit provided below the sample support means and capable of quickly cooling the sample which has arrived thereat, and an electromagnetic wave irradiation means provided above the cooling unit and capable of irradiating an electromagnetic wave on the sample which has passed across the irradiation means.

In the freezing method and apparatus, when the liquid contained in the sample is water, the electromagnetic waves may be microwaves or IR rays.

In the practice of the invention, attention has been paid, for example, to the hydrogen bond of water molecules which is one of the crystal growth factors in the sample. Immediately after this bond is disturbed by means of an electromagnetic wave, the temperature of the sample is quickly lowered. As a result, the growth of ice crystals is prevented and the distance into the sample in which water is amorphously frozen is significantly widened. More particularly, when electromagnetic waves are irradiated on a sample attached to the sample support means, the molecule movement of a liquid, such as water, contained in the sample is excited by the action of the electromagnetic waves, so that the hydrogen bond of water molecules is transiently disturbed. The sample held at the sample support means reaches the cooling unit, whereupon it is quickly cooled and frozen. Since the hydrogen bond of water in the sample is disturbed, the growth of the crystals is impeded and the liquid is solidified amorphously.

It will be noted that the term "amorphous solid" is intended to mean both a purely amorphous solid material and a crystalline solid material whose crystal size is not larger than 20 nm and which can be regarded as amorphous through observation with an electron microscope.

The above and other objects, features and advantages of the present invention will become more apparent from the following description taken in conjunction with the accompanying drawings.

DESCRIPTION OF THE PREFERRED EMBODIMENT

A freezing method and apparatus according to a preferred embodiment of the invention is described.

Figure 1:
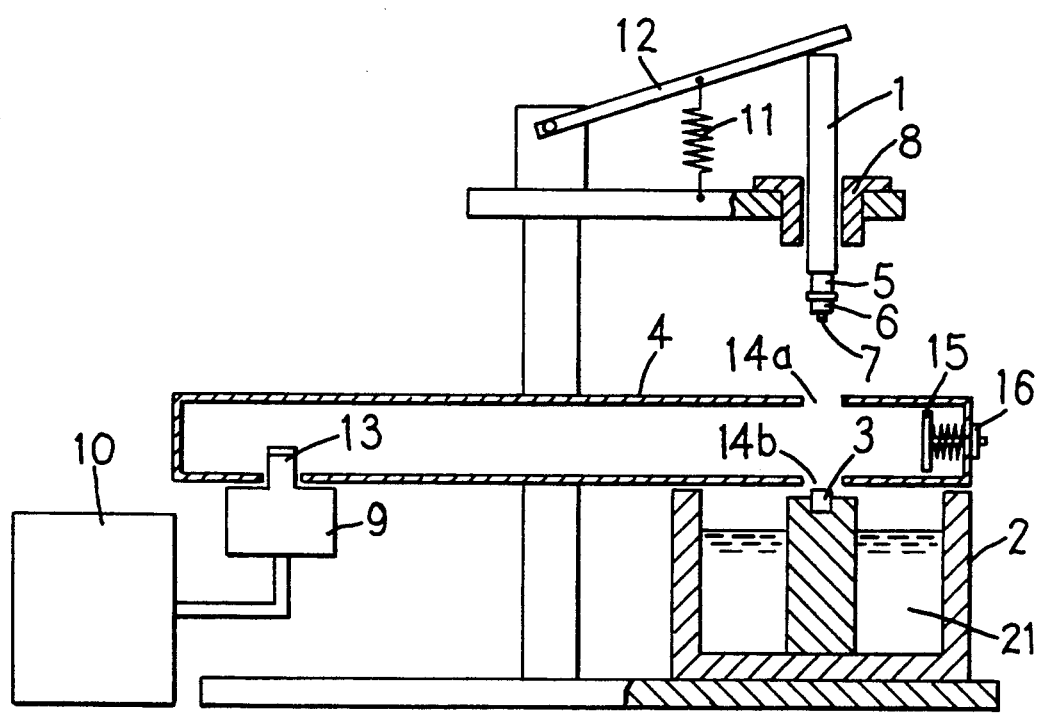
FIG. 1 is a schematic view of a freezing apparatus according to the invention.
Figure 3:
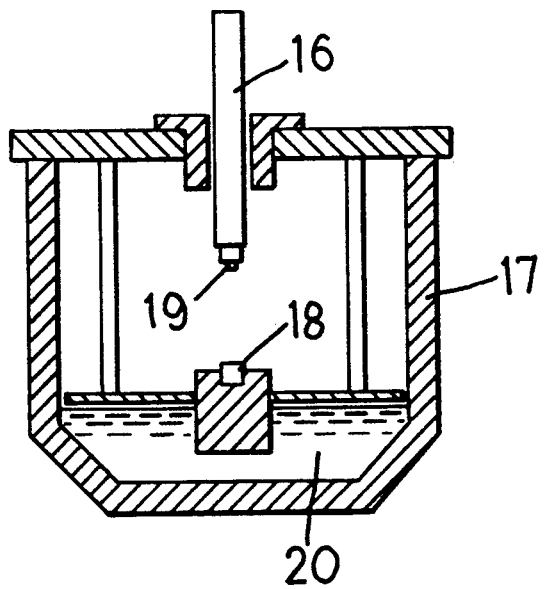
FIG. 3 is a schematic view of a known freezing apparatus.

A freezing apparatus embodying the invention is shown in FIG. 1. The apparatus of the invention has fundamentally a construction similar to that of the known apparatus shown in FIG. 3, wherein an organism sample piece or sample 7, which has been attached to a tip of a plunger 1 used as a sample support means, is press contacted with a cooled copper block 3 in a Dewar 2 and is thus quenched.

At the tip of the plunger 1 is provided a first damper 5 which is an air damper and which has at its tip thereof a second damper 6 attached to the sample 7. The second damper 6 may be a block such as, for example, of foamed silicone gel. The plunger 1 is guided by a linear bearing 8 and dropped vertically from the position shown in FIG. 1, and may be elevated. The initial dropping velocity is regulated by means of a link 12 biased by a spring 11.

A cooling unit is provided below the plunger 1 in order to quench the sample 7. The cooling unit has a Dewar 2 filled with a refrigerant 21 and the copper block 3, which is cooled by the refrigerant 21, has a flat upper surface.

A means for irradiating electromagnetic is disposed along the path on which the sample 7 and the copper block 3 travel by the dropping of the plunger 8. In the embodiment shown in the figure, the electromagnetic wave irradiation means includes a conductive waveguide 4 located above the copper block 3 and an electromagnetic wave generator 9. The generator 9 has an electromagnetic wave emitter 13 which is located at the left end of the waveguide 4 as shown in FIG. 1. The electromagnetic generator 9 is driven by a power supply 10. The waveguide 4 has throughholes 14a, 14b which are provided just above the copper block 3 and of the a minimum size neccessary for passing the tip of the plunger 1. When the plunger 1 is dropped, the sample 7 can reach the upper surface of the copper block 3 through the through-holes 14a, 14b.

In view of the properties of the waveguide 4, irradiation of the sample 7 with electromagnetic waves emitted from the electromagnetic wave emitter 13 is possible only when the sample is located between the throughholes 14a and 14b of the waveguide 4. Even when the electromagnetic generator 9 is continuously driven, no irradiation takes place when the sample is above the hole or after completion of the freezing.

In the waveguide 4 at the right end of FIG. 1, a movable wall 15 is provided which can be horizontally moved by means of a position adjuster 16 as viewed in FIG. 1. Electromagnetic waves at frequency emitted from the electromagnetic emitter 13 of the electromagnetic generator 9 become stationary waves in the waveguide 4 after superposition with reflected electromagnetic waves at the movable wall 15. The adjustment in position of the movable wall 15 with the position adjuster 16 depends on the wavelength of the electromagnetic waves can maximize the intensity of the electric field irradiated on the sample 7 passed through the through-holes 14a, 14b.

The electromagnetic waves irradiated on the sample are, for example, microwaves, infrared rays and the like whose wave lengths are properly selected depending on the type of liquid to be solidified, thus showing a satisfactory irradiation effect. Where the liquid is water, which is most common, microwaves having a frequency of 2.45 GHz can be used. The refrigerant used in the cooling unit may be not only liquefied gases such as liquid nitrogen, but also cooling media transferred through heat exchangers. The heat transmission with the sample 7 may be, aside from the metal contact system using the copper block 3, direct immersion in or application to liquefied gases or cooled gases.

The procedure for carrying out the freezing method of the invention by operation of the above apparatus is described below.

(I) Preparation

Liquid nitrogen is filled in the Dewar 2 to cool the copper block 3.

(II) Attachment of Sample

The second damper 6, having the sample attached at the tip thereof, is attached to the tip of the first damper 5. The material for the second damper may be foamed silicone gel (having a diameter of 100 and a thickness of 3 mm). The size of the sample is most appropriately 3 mm square and may be in the range of 1 mm to 5 mm square.

(III) Emission of Electromagnetic Waves

A magnetron (output power of 600 W, oscillation frequency of 2.45 GHz) was used as the electromagnetic wave generator and the power supply 10 was turned on to cause electromagnetic waves to be emitted from the electromagnetic wave emitter 13 into the waveguide.

(IV) Freezing of Sample

The plunger 1 descends by gravity and the resilience of the spring 11 attached to the link 12. During the passage of the sample, which is attached at the tip of the plunger, in the waveguide 4 (passing time is about 50 milli-seconds), microwaves are irradiated to excite the molecules of water in the sample 7. In this condition, the plunger further descends until the sample is press contacted with the cooled copper block thereby quickly freezing it.

(V) Termination of Electromagnetic Wave Emission

The power to the electromagnetic generator 9 is terminated.

(VI) Removal of The Sample

The plunger 1 is quickly pulled up and the frozen sample 7 is collected and kept in liquid nitrogen (not shown), completing all of the operations.

Figure 2A:
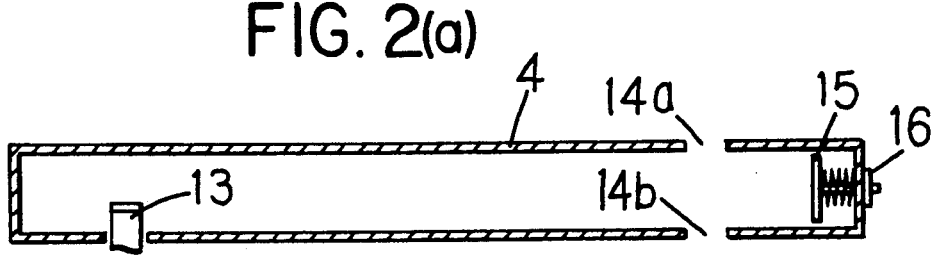
FIG. 2(a) is a side view, in longitudinal section, of a waveguide used in the freezing apparatus.
Figure 2B:
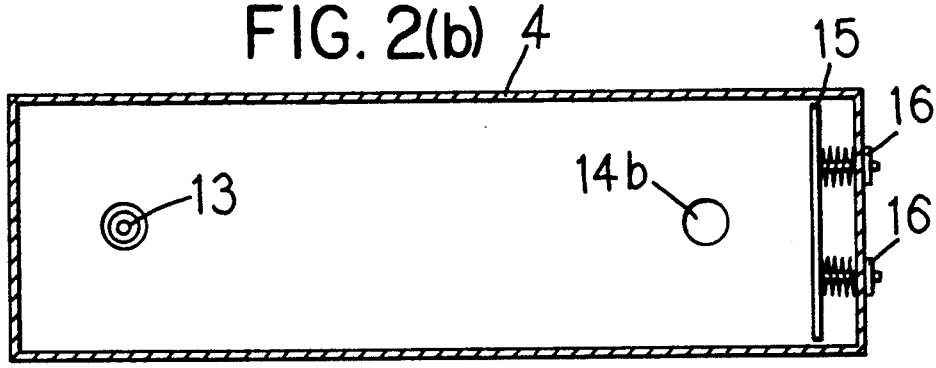
FIG. 2(b) is a plan view, in cross section, of the waveguide used in the freezing apparatus.

The shape of the waveguide which has been used in practical applications is described. The waveguide used is a rectangular waveguide as shown in FIG. 2. The reason for this is that it design is simple and electromagnetic waves can be readily carried. In the figure, reference numeral 13 indicates an electromagnetic wave emitter of electromagnetic generator 9 and reference numerals 14a, 14b, respectively, indicate through-holes through which the tip of the plunger 1 attached with the sample 7 are passed. In view of the properties of the waveguide 4, it is known that the amount of electromagnetic waves that leak from the through-holes 14, 14b to the outside is small. The movable wall 15 provided at the right end, as viewed in the figure, is connected to the position adjuster 16, by which the position of the wall is adjusted, so that the intensity of the electric field of the electromagnetic waves becomes maximized in the vicinity of the through-holes 14a, 14b.

More particularly, the plunger 1 used has a diameter of 12 mm and is made of Derlin resin (acetal resin), the Dewar 2 is made of foamed styrol resin with an inner capacity of 500 ml, the copper block 3 has a diameter of 15 mm and a length of 15 mm and is made of pure copper with a purity of 99.99%, and the waveguide is made of a 0.5 mm thick copper sheet. The waveguide has a size of 340 mm in length, 105 mm in width and 40 mm in height. The horizontal distance between the electromagnetic emitter 13 and the through-holes 14a, 14b is 295 mm and the diameter of the through-holes is 20 mm.

Using the above apparatus, the liver of mouse frozen according to the above procedure was observed through an electron microscope. The frozen sample was treated by freeze and substitution with acetone, embedding with Epon, ultrathin sectioning and uranium lead double dyeing. This procedure was carried out according to the method described in Preparation Method of Electron-microscopic Samples, edited by The Japanese Association of Electron Microcscope.

The results of the observation revealed that no crystals of ice were found at a distance of about 20 um from the surface of the sample which contacted the metal block. Although very fine ice crystals were present in a depth of 40 um, that portion was frozen in a state of not impeding the microscopic observation.

As will be apparent from the above results, in the case of water contained in organism samples, it is essential in the prior art to use liquid helium as a refrigerant in order to increase the freezing rate for obtaining an amorphous frozen state in a sample for a distance of approximately 20 um from the heat radiation surface at the time of freezing of the sample or from the contact of the sample surface with the copper block. In contrast thereto, according to the above example of the invention, a substantially amorphously frozen state could be obtained in a sample at a distance um of 40 from the surface of sample at a freezing rate as attained by liquid nitrogen.

Thus, according to the invention, the freezing region generating amorphous ice can be more readily and more significantly extended than that attained by known freezing methods and apparatuses.

Although the invention has been described in its preferred form with a certain degree of particularity, it is to be understood that many variations and changes are possible in the invention without departing from the scope thereof.

What is claimed is:

1. A method of quickly freezing a liquid-containing sample, said method comprising the steps of: subjecting said sample to irradiation with an electromagnetic wave and freezing said sample immediately after said irradiation at a temperature sufficient to form amorphous solid ice therein.

2. A method according to claim 1, wherein said electromagnetic wave is a microwave.

3. A method according to claim 1, wherein said electromagnetic wave is an IR ray.

* * * * *